United States Patent [19]

Niinobe et al.

[11] 4,256,550
[45] Mar. 17, 1981

[54] METHOD FOR PRODUCING VITAMIN $B_1$ AND ITS INTERMEDIATE

[76] Inventors: Takao Niinobe, 2209-5, Aza-Kamomukai, Oaza-Mii, Hikari; Kokichi Yoshida, 2839-1, Oaza-Murozumimura, Hikari; Masao Yokoyama, 14-10, Nijigaoka 4-chome, Hikari, all of Japan, 743

[21] Appl. No.: 97,341

[22] Filed: Nov. 26, 1979

[30] Foreign Application Priority Data

Dec. 1, 1978 [JP] Japan .................. 53/149419

[51] Int. Cl.³ .................. G25B 3/02; C25B 3/04
[52] U.S. Cl. .................. 204/72; 204/78
[58] Field of Search .................. 204/72, 78

[56] References Cited

U.S. PATENT DOCUMENTS 4,149,941  4/1979  Mitzlaff et al. .................. 204/72
4,176,020  11/1979  Misumi et al. .................. 204/72

Primary Examiner—R. L. Andrews
Attorney, Agent, or Firm—Burgess, Ryan and Wayne

[57] ABSTRACT

N-[2'-methyl-4'-aminopyrimidyl-5'-]methyl-4-methyl-5-β-hydroxyethyl-thiothiazolone(2) is electrochemically oxidized to produce vitamin $B_1$ in the anode side and simultaneously 2-methyl-4-amino-5-cyanopyrimidine is reduced to produce 2-methyl-4-amino-5-aminomethyl-pyrimidine in the cathode side. Both anode and cathode sides are separated from each other by at least one sheet of cation exchange membrane.

5 Claims, 1 Drawing Figure

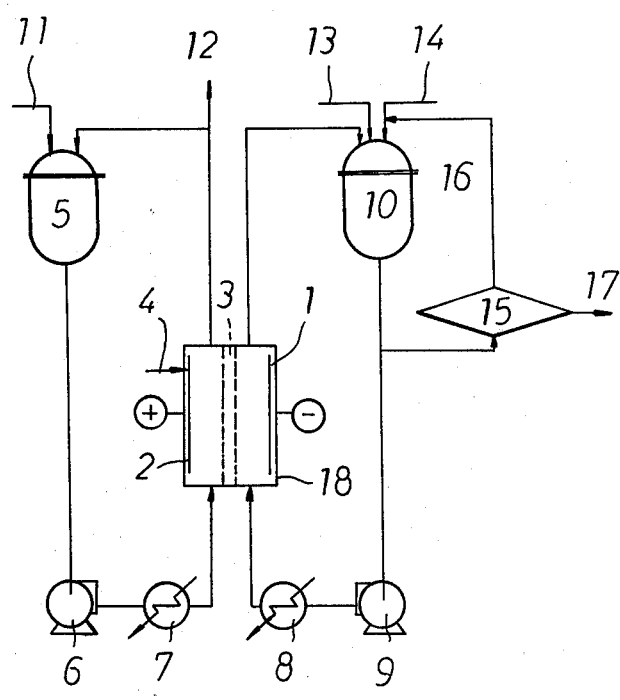

METHOD FOR PRODUCING VITAMIN B₁ AND ITS INTERMEDIATE

The present invention relates to a method for producing vitamin $B_1$ and its intermediate, and an apparatus therefor.

There have been conventionally known a method of electrochemically oxidizing N-(2'-methyl-4'-aminopyrimidyl-5')-methyl-4-methyl-5-$\beta$-hydroxyethyl-thiothiazolone(2) (hereinafter called "$SB_1$") to produce vitamin $B_1$, and a process for electrochemically reducing 2-methyl-4-amino-5-cyanopyrimidine (hereinafter called "C.P.") to obtain 2-methyl-4-amino-5-aminomethylpyrimidine (hereinafter called "D.P."), an intermediate for producing vitamin $B_1$ (The specifications of Japanese Pat. Nos. 133,464, 172,429, and 174,168, and Japanese Patent Publications Nos. 5019 of 1951 and 3977 of 1951).

These methods, however, are designed to carry out anodic oxidation and cathodic reduction reactions separately, and, in practice, turn out to be unsatisfactory in that electrical energy is consumed wastefully on the opposing electrode, and in that installation of individual reaction facilities is itself inefficient economically.

The present inventors, after having made considerable research in view of the drawbacks mentioned above, have come to completion of an industrially, highly favored method capable of simultaneously conducting both of the oxidation and reduction reactions on the cathode and anode sides, respectively.

It is therefore the object of this invention to provide a method and an apparatus for electrochemical production of vitamin $B_1$ and D.P. by simultaneous reactions in both electrode sides in which $SB_1$ is oxidized in the anode side and C.P. is reduced in the cathode side.

This invention is directed to a method for producing vitamin $B_1$ and its intermediate which comprises separating the anode side from the cathode side by at least one sheet of cation-exchange membrane, and oxidizing electrochemically N-[2'-methyl-4'-aminopyrimidyl-5'-methyl-4-methyl-5-$\beta$-hydroxyethyl-thiothiazolone(2) in an acidic solution in the anode side with the surface potential of the anode being maintained at not higher than the oxygen-generating potential so as to allow vitamin $B_1$ to be produced, while reducing electrochemically, at the same time, 2-methyl-4-amino-5-cyanopyrimidine in an acidic solution in the cathode side to allow 2-methyl-4-amino-5-aminomethylpyrimidine to be produced.

Another aspect of this invention is directed to an apparatus for electrochemically producing vitamin $B_1$ and its intermediate, which comprises an anode chamber for receiving an acidic solution of N-[2'-methyl-4'-aminopyrimidyl-5'-]-methyl-4-methyl-5-$\beta$-hydroxyethyl-thiothiazolone(2), a cathode chamber for receiving an acidic solution of 2-methyl-4-amino-5-cyanopyrimidine, and a separate chamber for receiving an acidic solution, the chamber being formed with two sheets of cation-exchange membranes.

The drawing is a flow diagram showing an outline of the method and apparatus according to the present invention.

In conducting simultaneously the organic electrolysis reactions at the anode and cathode, the greatest difficulty lies in how the electrochemical conditions at both electrodes should be made fully consistent with each other, while detailed investigations are required on prevention of intermixing of the electrolytes and organic substances at both electrodes as well as on individual oxidation and reduction reactions.

In the oxidation reaction of $SB_1$ at the anode, it has become evident from out experimental results that the selectivity and yield of the reaction, though depending on material of construction of the electrode and the composition of the electrolyte, are greatly influenced particularly by the surface potential of the electrode, and maintenance of the accurate electrode potential has proven to be of the primary requirement for realization of the process.

More specifically, in case the constant current reaction is effected in the electrolytic oxidation reaction of $SB_1$, generally, the anode potential increases with consumption of $SB_1$, and reaches eventually the oxygen-generating potential, leading to a marked decrease in the yield due to the lowered current efficiency toward the last stage of reaction and increased formation of by-products such as fluorescent substances.

Therefore, it is indispensable to improvement in the yield and in current efficiency to carry out the oxidation under control of the electrode potentials while maintaining the anode potential at not higher than the oxygen generating one. The appropriate potential varies depending on the anode material employed.

The anode material may be any material which is acid-resistant; for example, carbon, rhodium, platinum, ruthenium and lead oxide ($PbO_2$) can be employed. From an industrial point of view, favorable is the use of an electrode consisting of carbon or an electrode coated with platinum, rhodium, ruthenium, etc. Among them, use of carbon is of great advantage, because it does not give rise to oxygen-generation in the course of reaction and no consumption of the electrode is observed, though the consumption is presumed.

The anode potential to be controlled may be any level which is not higher than the oxygen-generating potential; in the case of platinum or in the case of an electrode coated with platinum, for example, especially preferred is the anode potential of $+0.9$ to $1.2^v$ and in the case of carbon is that of $+0.6$ to $1.1^v$, with reference to the saturated Calomel electrode (hereinafter called "S.C.E.").

The anolyte may be any one which is acidic with a mineral acid, and the one acidified with sulfuric acid, among others, is excellent in terms of the yield.

In order to prevent formation of by-products and intermixing with the catholyte in the course of the reaction, it has been found effective to keep the two electrode chambers separated from each other by the use of a cation exchange membrane.

On the other hand, the electrolytic reduction of C.P. on the cathode side is effected by the use of palladium under acidic conditions with a mineral acid. Palladium is generally utilized in the form of a palladium-coated electrode and, if desirable, may be employed in the form of an electrode plate of a palladium-containing alloy such as Pd-Ni alloy. The coating can be easily carried out by adding a palladium salt such as palladium chloride to the catholyte and energizing to allow Pd to deposit on the cathode. As a base material for the cathode in such a case, for example, utilized conveniently are platinum, silver, carbon, etc. In such an electrolytic reduction reaction, when compared with the electrolytic oxidation reaction of $SB_1$, the effect exerted by the electrode potential is relatively minor, and the electrode potential, though varying with the concentration of unreacted C.P., can be kept comparatively stable through maintenance of the current density. And, it has been found effective to add palladium chloride for the purpose of further stabilization thereof.

However, when the concentration of unreacted C.P. is lowered extremely with progress of the reaction, there takes place a remarkable decrease in the current efficiency, as is the case with $SB_1$, together with a marked drop resulted of the yield due to increased formation of by-products such as a hydroxymethyl compound and hence, it is effective and economical to suspend the reaction at the time when the conversion rate reaches 70 to 80% and to recover by separation the unreacted starting materials.

As the results of the research study by the present inventors, it has been proven that the oxidation at the anode and reduction reaction at the cathode can be allowed to proceed simultaneously.

Taking into consideration the electrochemical, optimal conditions of both reactions, it is desirable not only to control preferentially the electrode potential on the anode side but also to maintain the current density and electrode potential on the cathode side within the fixed ranges, respectively. In one embodiment with a Pt-Ti plate employed as a cathode, for example, it has been found out that the preferred current density be 2.5 to 15.0 $A/dm^2$, with the electrode potential being $-0.2$ to 0.4 v. Moreover, further study has revealed that the concentration of unreacted $SB_1$ governs the current density in oxidation reaction in the anode side, and it follows that by adjusting the concentration of unreacted $SB_1$, the current density can be controlled which enables to fulfill the electrochemical conditions of the cathode side and to make compatible the reactions in both of the electrode sides.

In the present invention, the anolyte and catholyte are to be kept separated and isolated by cation exchange membranes. As the cation exchange membrane may be employed those having a sulfonic acid group or a carboxylic group, preferably a strong acidic cation exchange membrane which is made the trade names of, for example, NEOSEPTA CL-25T, CH-45T, C66-5T (Tokuyama Soda Co., Ltd., Yamaguchi, Japan) and SELEMION CMV ( Asahi Glass Co., Ltd., Tokyo, Japan). Since $SB_1$ leaked from the anolyte into the catholyte inhibits the reduction reaction at the cathode, the exchange membranes are preferably those not allowing cations of 200 or more in molecular weight to permeate.

The cation exchange membrane may be employed in one sheet, and it may be, if desired, employed in plural, preferably two sheets, wherein there is formed between these membranes a separate chamber into which an acidic solution is filled to thus effect electrolysis, and the solution in the separate chamber may be intermittently or continuously checked to prevent penetration of undesirable components from the anode and cathode chambers, for example, possible permeation of $SB_1$.

In accordance with the present invention, in this way, the electrolytic oxidation and the electrolytic reduction can be carried out simultaneously and efficiently. In addition, when the electrolytic reduction alone is carried out as in the conventional process, evolution of chlorine is inevitable in case chlorine ions exist in the electrolytic solution, whereas, in accordance with the present invention, such an air pollution can be avoided.

The method according to the present invention can be applicable, whether it may be conducted batch-wise or in a continuous manner. The present invention will be more specifically described below with the examples, which, however, are not intended to restrict the invention.

ELECTROLYTIC BATH AND APPARATUS EMPLOYED IN THE EXAMPLES

The descriptions will be given below by means of the drawing:

In the drawing, numeral 18 designates an electrolytic bath; numeral 1 a cathode; numeral 2 an anode; numeral 3 two sheets of cation exchange membranes; numeral 4 a Rugin pipe; numeral 5 a relay vessel for an anode chamber; numerals 6 and 9 circulating pumps; numerals 7 and 8 heat exchangers; numeral 10 a relay vessel for a cathode chamber; numeral 11 a feeding passage for $SB_1$; numeral 12 a discharging passage for vitamin $B_1$; numeral 13 a feeding passage for palladium chloride; numeral 14 a feeding passage for C.P.; numeral 15 a recovery step for C.P.; numeral 16 a feeding passage for recovered C.P.; and numeral 17 a discharging passage for D.P. Surface area of each of the electrodes is 4 $dm^2$, and a anode potential is controlled by the constant potential device.

PRETREATMENT OF THE CATHODE

In advance of the reaction, a solution of $PdCl_2$ (0.5 g in Example 1, and 0.6 g in Example 2) in an 8% HCl solution is placed in the cathode chamber, to allow palladium to deposit on the cathode at a current density of 0.2 $A/dm^2$.

The solutions in both of the electrode chambers are subjected to forced circulation by means of pumps (flow rate of 5 to 10 cm/sec), while cooling is effected through heat exchangers installed outside 7 and 8.

EXAMPLE 1

The electrolysis apparatus as aforementioned is employed using NEOSEPTA CL-25T (trade name of a strongly acidic cation exchange membrance produced by Tokuyama Soda Co., Ltd., Japan) as the cation exchange membrances, and reaction is effected with the anode potential controlled at 1.1$^v$ against s.c.e. at a reaction temperature of 10° C. under the charging conditions as described below:

|  | Cathode side | Anode side |
| --- | --- | --- |
| Electrode plates | Pt-Ti Plate[1], 4 $dm^2$ | Pt-Ti plate, 4 $dm^2$ |
| Raw materials charged | C.P.44.7g, $PdCl_2$ 0.45g | $SB_1$ 71.4g |
| Electrolytic solutions | 8% HCl 1000 ml | 5% $H_2SO_4$ 500 ml |

The separate chamber formed with the cation exchange membranes is filled with 3% $H_2SO_4$.

The current density at the time of initiation of the reaction is 2.8 $A/dm^2$. Shown in the following are analytical values, along with the current efficiencies, as determined by high-speed, liquid chromatography 4.5 hours after the reaction is initiated:

|  | Cathode side | Anode chamber |
| --- | --- | --- |
| Products in the reaction solutions | D.P. 33.2 g | Vitamin $B_1$[2] 67.5g |
| Unreacted raw materials | C.P. 11.4 g | $SB_1$. 10.8g |
| Conversion ratios | 72.7% | 83.3% |

-continued

| | Cathode side | Anode chamber |
|---|---|---|
| Current efficiencies | 78% | 98% |

REMARKS (1) Pt-Ti plate: Ti plate (thickness of 2 mm) coated 2μ thick with Pt.

(2) Quantitatively determined as vitamin $B_1$ hydrochloride salt.

EXAMPLE 2

With carbon plates (4 dm²) employed as the electrode plates in place of the Pt-Ti plates in Example 1, the raw materials are added during reaction in succession as shown in the following Table, while the reaction temperature is maintained at 10° C., and the anode is controlled at the electrode potential of 0.9ᵛ against S.C.E.:

| | Cathode side | Anode side |
|---|---|---|
| Charged amount of raw materials at the initiation of reaction | C.P. 30g, $PdCl_2$ 0.3g | $SB_1$ 22.5g |
| Electrolytic solution | 8% HCl 1000 ml | 1% $H_2SO_4$ 500ml |
| Raw materials added over a 5-hour period after the initiation of reaction | Total of C.P. 30.5g/5 HR | Total of $SB_1$ 75 g/5 HR |
| $PdCl_2$ | 10 ml of 8% HCl contg. 2% $PdCl_2$ added over a 1 hr. period between 3.5 and 4.5 hrs. after the initiation. | |

The current density at the time of initiation of electrolysis is 3.1 A/dm². Shown in the following Table are analytical results and current efficiencies on the reaction solution taken at the time of 4 hours after the initiation of the reaction:

| | Cathode side | Anode side |
|---|---|---|
| Products in the reaction solutions | D.P. 44.2 g | Vitamin $B_1$ 83.0 g |
| Raw materials | C.P. 15.5 g | $SB_1$ 12.6 g |
| Conversion ratios | 71% | 85% |
| Current efficiencies | 74% | 98% |

EXAMPLE 3

In this example a continuous production method is explained. Referring to the drawing, each of the raw material solutions is continuously fed into the anode chamber and cathode chamber through the route of 11, 5, 6 and 7 or that and 14, 10, 9, and 8, and continously cycled to 5 and respectively 10. Excess volume of the solution in each of the chambers is discharged from 12 or through 10 and 15, from 17 to maintain the solutions at both of the chambers in constant volumes.

REACTION CONDITIONS

Electric current value; 7 A/dm² (constant current),
Electrode; Pt-Ti plate, 4 dm² as in Example 1,
Reaction temperature; 10° C.±1° C. in the cathode side, 25° C.±1° C. in the anode side,
Cycle volumes of electrolytes; anolyte, 1.5 L., Catholyte, 1.5 L., Compositions of solutions in the cathode side and anode side at the initiation of the reaction;

| Cathode side | Anode side |
|---|---|
| C.P. 1.5 w/v % (22.5 g/3% HCl, 1,500m3) | $SB_1$ 6 w/v % (90 g/2.5% $H_2O$, 1,500 ml) |

Composition of the solution filled at the separate chamber formed with the two membranes; 2% $H_2SO_4$.

Compositions of solutions fed into the cathode side and anode side;

| | Cathode side | Anode side |
|---|---|---|
| Concentrations of raw materials | C.P. 8 w/v % | $SB_1$ 20 w/v % |
| Total acid concentrations | 7 w/v % | 6 w/v % |

| Volumes of solutions fed and discharged; | | |
|---|---|---|
| | Cathode side | Anode side |
| Volume of feed and discharge solutions | 420 ml/hr. | 369 ml/hr. |

(In order to maintain the volumes of the cycling solutions in constant amounts, both of the volumes of feed and discharge solutions are equalized with each other.)

In advance of the reaction, the cathode plate is coated with palladium in a catholyte of 3% HCl containing 1.2 g of $PdCl_2$ at the current density of 0.1 A/dm² at 10° C., employing 2% $H_2SO_4$ as both of the anolyte and a solution filled in the separate chamber formed with the two ion-exchange membranes. Cycling rate of the solutions:

The superficial velocities of the cycling solutions in both of the cathode and anode sides are maintained at 30 cm/sec. and that of the solution in the separate chamber at 5 cm/sec. so as to make the pressure of the separate chamber rather higher than those of the cathode and anode sides.

Under the raction conditions mentioned above the reaction was carried out for 20 hours and the following result was obtained.

| | Cathode side | Anode side |
|---|---|---|
| Products in the reaction solutions | D.P. 546 g | $V.B_1$ 1139.1 g |
| Unreacted raw materials | C.P. 147.9 g | $SB_1$ 534.1 g |
| Conversion ratios | 79% | 66% |
| Current efficiencies | 76% | 97% |

We claim:

1. An electrolytic method for simultaneously producing vitamin $B_1$ and 2-methyl-4-amino-5-aminomethylpyrimidine which comprises providing an electrolysis cell separating the anode side of said cell from the cathode side by at least one sheet of cation-exchange membrane, and oxidizing electrochemically N-[2'-methyl-4'-aminopyrimidyl-5'-]methyl-4-methyl-5-β-hydroxyethyl-thiothiazolone(2) in an acidic solution in the anode side with the surface potential of the anode being maintained at not higher than the oxygen-generating potential so as to allow vitamine $B_1$ to be produced, while reducing electrochemically, at the same time, 2-methyl- 4-amino-5-cyanopyrimidine in an acidic solution in the cathode side to allow 2-methyl-4-amino-5-aminomethylpyrimidine to be produced.

2. A method according to claim 1 wherein the oxidation in the anode side is carried out in an acidic anolyte with a mineral acid, preferably with sulfuric acid and the reduction in the cathode side is effected by the use of palladium under acidic conditions with a mineral acid.

3. A method according to claim 1 wherein the anode is made of carbon, one member of the group consisting of platinum, rhodium and ruthenium, or a material coated with one of the said group, and the cathode is made of a material coated with palladium or an alloy containing palladium.

4. A method according to claim 1 wherein the oxidation in the anode side is carried out with the surface potential of the anode being maintained from +0.6 to 1.1$^v$, with reference to the saturated Calomel electrode, using a carbon anode.

5. A method according to claim 1 wherein the oxidation in the anode side is carried out with the surface potential of the anode being maintained from +0.9 to 1.2$^v$, with reference to the saturated Calomel electrode, using a platinum anode or a platinum-coated anode.

* * * * *

UNITED STATES PATENT AND TRADEMARK OFFICE
CERTIFICATE OF CORRECTION

PATENT NO. : 4,256,550

DATED : March 17, 1981

INVENTOR(S) : Takao Niinobe, et al

It is certified that error appears in the above—identified patent and that said Letters Patent is hereby corrected as shown below:

Column 3, line 45: "leaked" should be --leakage--.

Column 4, line 22: "the" should be --a--.

Column 5, line 58: "or" should be --and--; after "8," insert --respectively,--; "continously" should be --continuously--. "and" (2nd occurrence) should be --of--.

line 62: "in" should be --at--.

Column 6, line 9: "1,500m3)" should be --1,500ml)--.

line 12: "at" should be --in--.

line 44: "raction" should be --reaction--.

Signed and Sealed this

Fifteenth Day of September 1981

[SEAL]

Attest:

GERALD J. MOSSINGHOFF

Attesting Officer     Commissioner of Patents and Trademarks